United States Patent [19]
Chevillon et al.

[11] Patent Number: 5,755,790
[45] Date of Patent: May 26, 1998

[54] INTRALUMINAL MEDICAL DEVICE

[75] Inventors: Gérard Chevillon, Montrouge; Guy Nadal, Poitiers, both of France

[73] Assignee: B. Braun Celsa, Chasseneuil, France

[21] Appl. No.: 631,079

[22] Filed: Apr. 12, 1996

[30] Foreign Application Priority Data

Apr. 14, 1995 [EP] European Pat. Off. ............ 95400850

[51] Int. Cl.⁶ ..................................................... A61F 2/04
[52] U.S. Cl. ................................ 623/12; 623/1; 606/200
[58] Field of Search ........................ 623/1, 11, 12; 604/4, 96, 104, 106; 606/194, 195, 198, 200

[56] References Cited

U.S. PATENT DOCUMENTS

| 4,425,908 | 1/1984 | Simon . | |
|---|---|---|---|
| 4,688,553 | 8/1987 | Metals . | |
| 4,990,156 | 2/1991 | Lefebvre . | |
| 5,108,418 | 4/1992 | Lefebvre | 606/200 |
| 5,300,086 | 4/1994 | Gory et al. | 606/200 |
| 5,344,427 | 9/1994 | Cottenceau et al. | 606/200 |
| 5,370,657 | 12/1994 | Irie | 606/200 |
| 5,375,612 | 12/1994 | Cottenceau et al. | 606/200 |
| 5,383,887 | 1/1995 | Nadal | 606/200 |
| 5,415,630 | 5/1995 | Gory et al. | 606/200 |
| 5,509,900 | 4/1996 | Kirkman | 606/198 |

FOREIGN PATENT DOCUMENTS

| 621016 | 10/1994 | European Pat. Off. | 623/1 |
|---|---|---|---|
| 2573646 | 5/1986 | France . | |
| 2580504 | 10/1986 | France | 606/200 |
| 2587901 | 4/1987 | France . | |
| 2649884 | 1/1991 | France . | |

Primary Examiner—Michael J. Milano
Assistant Examiner—Tram Anh T. Nguyen
Attorney, Agent, or Firm—Rothwell Figg Ernst & Kurz

[57] ABSTRACT

The invention generally relates to an intraluminal medical device, that is to say a device intended to be implanted in a passage in the body. This device has a substantially "filiform" structure with elongated legs (11) which have no hooks for anchoring them to the passage. These legs comprise two portions (11a, 11b). The first portion (11a) which bears against the passage has a flattened and substantially solid surface. At right-angles to the main axis (13) of the device, the maximum dimension of the second portion (11b) is less than that of the first portion.

Application particularly to temporary/definitive filters.

13 Claims, 2 Drawing Sheets

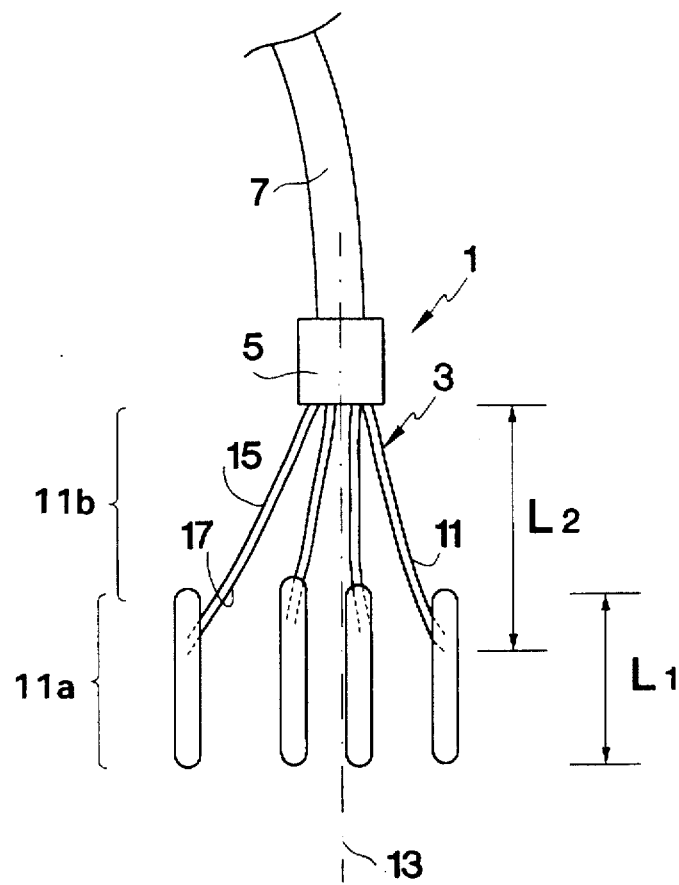
FIG. 1
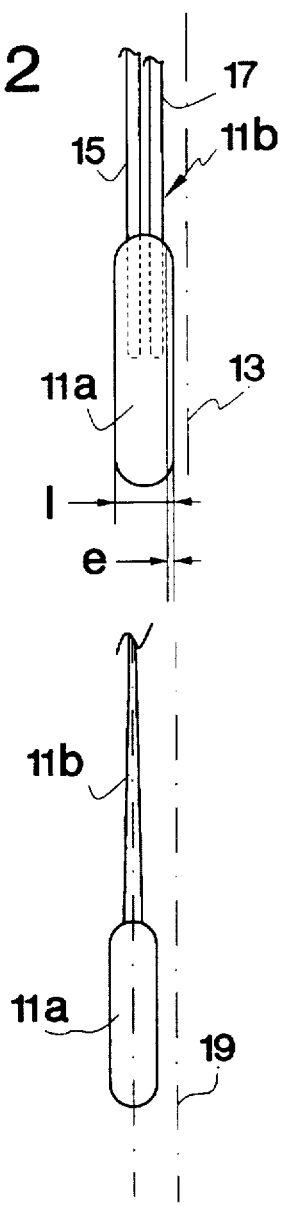
FIG. 2
FIG. 3
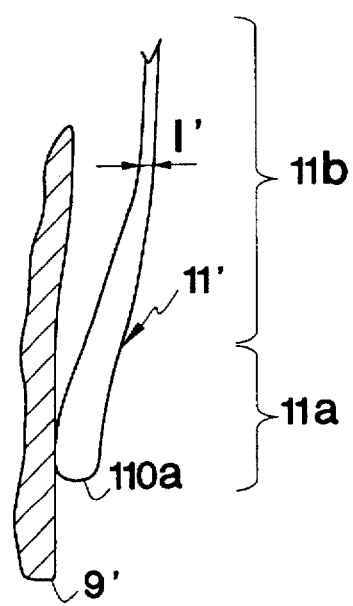
FIG. 4

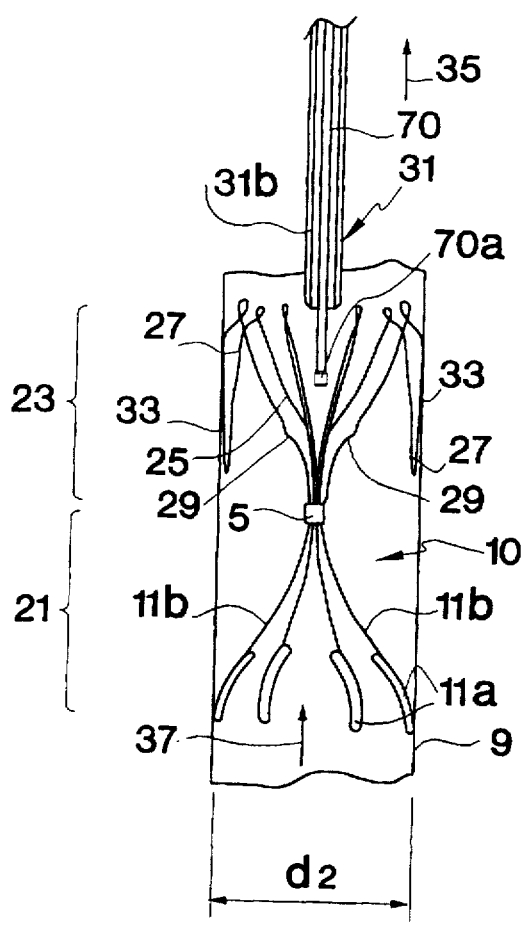
FIG. 5
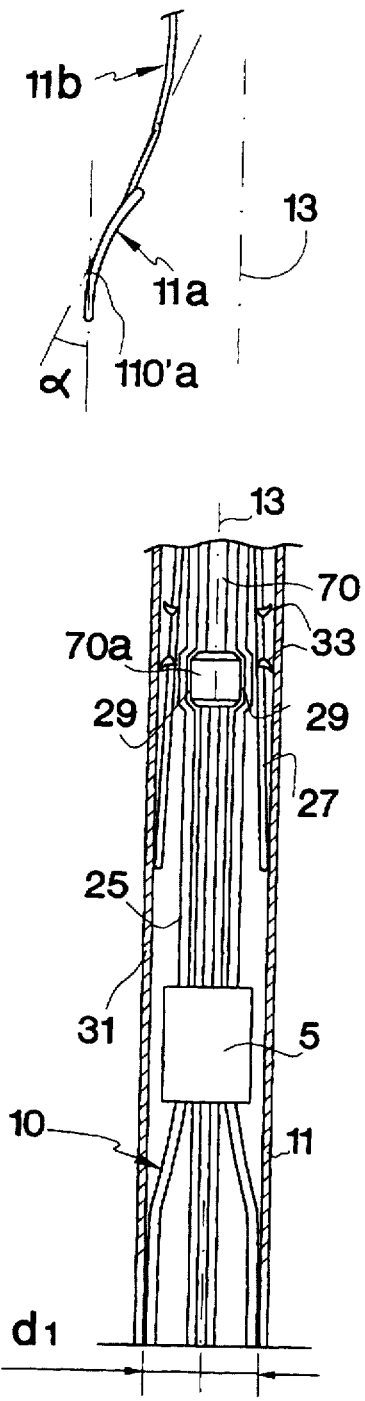
FIG. 6
FIG. 7

INTRALUMINAL MEDICAL DEVICE

FIELD OF THE INVENTION

The invention relates generally to an intraluminal medical device, that is to say one which is intended to be implanted in a passage in the body. This device has a substantially "filiform" structure, having a main axis, adapted to occupy a first reduced diameter in a radially folded-in state of the device (so allowing it to be implanted) and a second widened diameter when the said device is implanted, and comprising elongated legs which, in this implanted state, comprise a first portion adapted to contact a wall of the passage and a second portion.

BACKGROUND OF THE INVENTION

FR-A-2 573 646 or U.S. Pat. No. 5,383,887 illustrate such a medical device; in that instance it is a filter intended to be placed in the path of blood in order to trap clots.

But these two filters are so-called "definitive" filters, that is to say intended to be implanted in an a priori permanent manner in the receiving organism without normally any possibility of removal. For this purpose, they are also provided with means of anchoring them to the wall of the receiving passage, such as hooks intended to penetrate the said wall.

Now, problems occur when it is desired to be able to implant filters and more generally intraluminal medical devices of the aforesaid type temporarily, allowing the practitioner to withdraw the device after a more or less prolonged period of implantation (a period which may be from one to a few weeks in the case of existing blood filters).

SUMMARY OF THE INVENTION

The problem addressed by the present invention is linked with the practical demands of use of such devices which must take into account:

- a problem of cellular development around the portion of the legs which is applied against the receiving passage, which development must not prevent withdrawal of the device at the end of temporary implantation,
- a problem connected with particularly the radial dimension of the device, taking into account the fact that it is desirable to be able to implant it through sheaths of the smallest possible diameter.
- and an additional concern regarding the flexibility which it is desirable that the legs should have, particularly in terms of the length of their so-called "second portion", in order to favour transformation of the device from its first reduced diameter to its second widened diameter with the desired flexibility and elasticity.

All these demands have so far proved difficult to reconcile. And no prior art known to the Applicants has hitherto taken them jointly into account.

That is why, with the object of providing a satisfactory solution to this situation, the invention proposes that:

- the first portion of at least some of the legs of the device has a flattened surface bearing substantially completely against the wall of the passage,
- substantially at right-angles to the main axis and in the folded-in state of the device, this first portion has a maximum dimension which is greater than that of the second portion, and
- the first portion is devoid of means of hooking onto the wall of the passage.

Thus, by virtue of this last-mentioned characteristic feature, it becomes possible perhaps to withdraw the medical device while by virtue of the first and second characteristic features, it is possible to provide both the flexibility and the limited bulk of the legs, so favouring implantation through a small diameter sheath and flexibility in handling the device while ensuring a favourable surface intended to bear against the wall of the passage.

Still with the intention of favouring flexibility and elasticity in the device and limiting its essentially radial bulk, the length of elongation of the first portion of the legs will preferably be less than that of the second portion.

In order further to favour withdrawal without adversely affecting the stability within the framework of a "temporary" implantation, another characteristic feature of invention provides for the flattened surface of the first portion to be capable of being curved along a direction substantially parallel with the general axis.

For industrial production of the device, a number of solutions have been proposed:

- production of the first and second portion in the manner of an integral plate (the width of this plate being progressively reduced from the free end of the first portion towards the second portion),
- production of these two portions which are still integral with one another but in the form of a substantially round filament (in the case of the second portion) and then a plate (for the first portion) or even in a plurality of parts with a first substantially plate-like portion and a second portion comprising a plurality of filaments.

After a difficult development, by reason of the aforesaid requirement with are in effect compatible with one another only with difficulty, another characteristic feature of the invention provides for the first portion to have a width between 0.7 mm 1.5 mm approx. with a thickness between approx 0.05 mm and 0.25 mm while the maximum dimension of the second portion will preferably be less than approx. 0.7 mm.

Particularly within the framework of a temporary blood filter, the invention furthermore envisages:

- that the legs at least partially develop into a substantially conical corolla around the said main axis, in the implanted state of the device,
- that these legs be joined to one another by a common head at one end of the second portion on the side on which the corolla has its smaller diameter,
- that the first portion be situated opposite this head and extend on the side of the corolla which is of the largest diameter,
- and that the said first and second portions extend in accordance with a common direction of elongation which is substantially rectilinear or which has a curvature of less than 90° (thus avoiding in particular the hairpin legs of FR-A-2 573 646). It should be noted that this last-mentioned characteristic feature could be used by itself.

In the already quoted case of blood filters, it should furthermore be noted that the invention is quite particularly interesting in the hypothetical case where the filter is first used temporarily and is then used finally in the interior of the receiving vessel.

In this field, EP-A-348 295 in particular has disclosed a filter adapted to be implanted by means of an implanting sheath, the said filter comprising not only first filtering means with elongated legs which have no means of hooking engagement on the vessel, second means of maintaining the said filtration means in position to allow the filter to be changed from a "temporary use" situation to one of "definitive use".

The same drawbacks as already mentioned in connection with FR-A-2 573 646 or U.S. Pat. No. 5,383,887 already exist in respect of EP-A-348 295.

And the solution according to the invention is again, in this case, that of providing for (at least) one maximum dimension of the essentially solid and flattened surface of the first portion of the "filtering" legs to be greater than the maximum dimension of the second portion, it of course being possible for the additional and already mentioned characteristic features to be provided. The quality of filtration (by a properly centred bearing application) and possible withdrawal will then be associated with the aforesaid features.

The same can be said in the hypothetical case where the filter which can possibly be used on a temporary or final basis is of the type disclosed in FR-A-2 718 949.

It will likewise be noted that the invention also relates to a method of producing the intraluminal medical device described hereinabove.

In accordance with a first embodiment, the leg portion will be made in one single piece from an elongated filament of rounded cross-section, one part of which will be flattened to constitute the first portion.

Alternatively, the first and second portions will be made respectively from one or a plurality of elongated filaments and a plate, said filaments and plate then being joined to one another for example by crimping or welding.

BRIEF DESCRIPTION OF THE DRAWINGS

That which follows provides a more detailed description of the invention on the basis of the appended drawings, in which:

FIG. 1 shows a first embodiment showing the resting state of an intraluminal blood filter intended exclusively for temporary use;

FIG. 2 shows a detail of the filter shown in FIG. 1;

FIGS. 3 and 4 each show an alternative embodiment of the leg segment illustrated in FIG. 2;

FIG. 5 shows a possible embodiment of a filter for temporary/definitive use;

FIG. 6 shows a detail of a leg of the filter shown in FIG. 5; and

FIG. 7 shows on an enlarged scale a part of the same filter in a radially folded-in condition.

DETAILED DESCRIPTION

Firstly, FIG. 1 illustrates an intraluminal filtration device 1 capable of being positioned by laying bare or preferably by the percutaneous route (the conventional so-called "Seldinger" method).

The device 1 comprises the auto-expansible blood filter 3 proper, of which the head 5 is connected to a biocompatible and flexible operating rod 7.

The filter 3 which has no means of anchoring to its receiving vessel (which could be the vessel 9 in FIG. 5) comprises a substantially filiform structure, that is to say with fine legs 11 elongated substantially in accordance with a general axis 13 when the filter is radially constrained, its legs therefore being substantially parallel with one another.

In the case in point, the filter takes the general form of a substantially conical corolla in its illustrated and radially unrestrained state, the legs 11 being regularly distributed around the axis 13 which is an axis of revolution. The legs 11, preferably between 4 and 8 in number, may be considered as comprising two portions, a first portion 11a and a second portion 11b. The portion 11a which terminates the legs on the larger diameter side of the corolla, allows the filter to come into contact with the vessel while the second portion 11b, apart from its filtering function, provides for the filter to be opened up into the form of a corolla or to be radially closed, extending more towards the interior of the cone when the corolla is opened out, without therefore coming particularly and a priori in contact with the vessel.

While the part 11a has a flattened form, the part 11b is finer. To be more precise, the enlarged view in FIG. 2 shows that when the filter is in its radially constrained condition which makes it possible for it to be implanted, the maximum dimension 1 at right-angles to the axis 13 of the flattened surface 11a is greater than that of the corresponding portion 11b so that the radial bulk of the part 11b is less than that of the part 11a.

Still in FIGS. 1 and 2, it will also be noted that on their terminal part 11a, the legs 11 substantially appear as a solid plate with a rounded perimetral edge while they take the form of a round filament over their length 11b, it being stipulated that advantageously the length $L_1$ of the portion 11a will be less than the length $L_2$ of the portion 11b on the axis 13.

Taking into account the functions which devolve upon them, the widened bearing portions 11a will extend on the side of the free end of greatest diameter when the filter is opened while the portions 11b will extend in accordance with a smaller diameter to the point where, in the case of the illustrations shown in FIG. 1, the two round filaments 15, 17 which form the portion 11b may be connected at the location of the holding head 5.

A tricky development has demonstrated that it is preferable for the width 1 of the "bearing portion" 11a to be between 0.8 mm and 1.2 mm, with a transverse thickness e between 0.1 and 0.2 mm, the maximum "transverse" dimension of the filaments 15, 17 of the second portion 11b (in the case in point, the diameter) being preferably between 0.2 mm and 0.5 mm, being for example 0.35 mm, this for a metal embodiment for example made from Phynox (registered Trade Mark) or any suitable stainless steel.

In the case of the hypothetical embodiment in FIGS. 1 and 2, the filaments 15, 17 and the plate 11a will constitute different parts; the filaments (which will preferably extend substantially parallel with one another) may be crimped or preferably welded on to the plate.

But in an alternative embodiment such as that illustrated in FIG. 3, it is possible to envisage producing each leg 11 with a portion 11b of a single round filament extended in integral fashion from by the portion 11a in the general direction of elongation of the leg identified by reference numeral 19 in FIG.3.

In order to ensure that the portion 11a is more flattened than the portion 11b, it is possible to proceed by localised flattening of the metallic wire used, for example by rolling or on the other hand by drawing or even by electrolysis.

It must however be noted that the embodiment shown in FIGS. 1, 2 and 3 shows a fairly abrupt widening of the legs between the portions 11b and 11a even if the legs thus constituted can still be considered as "filiform".

On the other hand, the filiform leg 11' shown in FIG. 4 has a width 1' which will increase progressively firstly along the second portion 11b and then the first terminal portion 11a which, in the case in question, is shown to be bearing against a passage wall 9'. In order to obtain such a form of "progressively widening" leg, it is possible in that case also to resort to a rolling or a drawing technique or even electrolysis with for example a thickness which progressively reduces as one approaches the free end 110a of the portion 11a.

FIGS. 5 and 7 now show the essential features of a filtration structure which can be used temporarily or definitively.

In FIG. 5, firstly, there is shown in a slightly different structural constitution, the filter 10 proper and its flexible operating rod 70.

Although the main blood filtering part of the filter 10 fairly closely resembles that of the filter in FIG. 1, with round filament legs (in the simple version) which are extended substantially axially by small elongated solid plates 11a and which develop generally according to a conical corolla from a head 5 which connects various proximal portions 11b, it can be seen that opposite this frontal filtering part 21 the filter has a second conical corolla 23, the two corollae being disposed head-to-tail and being connected by the head 5.

The main function of the second corolla 23 is to ensure that the filter when finally implanted is held in place. It is made from (a) filament(s) and still has two portions, a first portion 25 developing substantially in a cone shape from the head 5 and then a second portion 27 of hairpin form defining kinds of centering shoes extending substantially parallel with the wall 9 when the filter is in the implanted condition.

For its connection to the operating rod 70, the filter 10 which is in this particular instance separable from the said rod, has furthermore crenellations 29 formed by localised deformation of the portions 25, the hollow in these deformed parts receiving a widened head 70a formed on the end of the rod 70 when the filter 10 is radially constrained inside the flexible introducing sheath 31, as is illustrated in FIG. 7.

In the enlarged view in FIG. 6, the flattened portion 11a has a shape which is curved inwardly from the corolla to follow a direction which is substantially parallel with the general axis 13 when, as has been assumed, the filter (and therefore its legs 11) are in the radially constrained state. The angle of curvature α is preferably between approximately 0° and 45°. It is then essentially the free terminal part 110' a of the portion 11a which will come to bear against the wall 9.

FIG. 7 shows the filter 10 with its legs 11, 25, 27, in a double head-to-tail corolla, each radially constrained according to the main axis 13 which in this case is also the axis of the sheath or implantation catheter 31 within which the filter is contained, with then a diameter $d_1$ (corresponding to the inside diameter of the catheter) which is less (within the scale) than that $d_2$ which is present when it is implanted inside the vessel 9 (see FIG. 5).

It should be noted in FIG. 7 that in this state of the filter which is ready to be implanted, the crenellations 29 receive the head 70a of the rod 70 which then makes it possible to operate the filter from outside the body according to the axis 13 in so far as (in conventional manner) the sheath 31 and the rod 70 have a sufficient axial length to extend between the outside of the body of the patient in question and the implantation vessel (which may in particular be the vena cava).

It should likewise be noted, as can be seen in FIG.5 and more clearly in FIG.7, that the appendices 27 comprise fixing means 33, in this case in the form of double inverted hooks which will make it possible to anchor the filter in the wall of the vessel in the event of definitive implantation.

The technique of implanting a filter, whether it be for temporary or final use, is indicated in the aforesaid publications or also in U.S. Pat. No. 4,990,156.

Generally speaking, after having made an incision through the patient's skin, an access route is formed as far as the vascular implantation area after which the introducing sheath 31 is slid therein so that it extends along the access route, its proximal end emerging from the body while its distal end reaches the implantation vessel. After having been radially constrained inside the sheath, in front of the operating rod, the filter is then pushed by this rod along the catheter as far as the distal end of the sheath (reference numeral 31b in FIG. 5). When this end is correctly positioned inside the vessel, a displacement of the sheath relative to the rod makes it possible to cause the filter to emerge, its legs naturally expanding in a corolla.

With the filter in FIGS. 5 and 7, it is possible in a first stage to have only emergence of the legs 11, the holding legs with their hooks 33 being held back inside the sheath where there is still co-operation between the crenellations 29 and the head 70a of the rod also allowing an advance or return movement of the filter. By reason of the fact that, in this position, only the first portions 11a (which have no anchoring hooks) come into contact with the wall of the vessel (and this over an essentially solid and fairly substantial surface area), it is possible after a few weeks to withdraw the filter by pulling this rearwardly via the rod 70 or by pushing the sheath forwards.

If on the other hand, at the end of this first period of implantation, the practitioner judges that the risks of an obstruction in the vessel are still present, he may decide on a definitive implantation of the filter. For this, he withdraws the sheath 31 rearwardly (arrow 35) while holding the filter in position so that the second corolla 23 opens out, the appendices 27 and their hooks 33 respectively applying themselves and becoming anchored in the wall of the vessel (FIG. 5). As the filter has thus been implanted (with of course its first corolla 21 disposed facing the flow of blood 37), the practitioner withdraws the sheath and the rod (thus of course already separated from the filter as FIG. 5 shows), this via the already used access route, the filter being left in the vessel.

We claim:

1. An intraluminal, blood filtering medical device configured to be positioned in a blood vessel within a body, said blood filtering medical device having a first, radially restrained configuration when in which said blood filtering medical device is insertable into said blood vessel by means of a rod extending through an implantation sheath and a second, radially expanded configuration when said blood filtering medical device is positioned within said blood vessel, said blood filtering medical device comprising:

a head portion that is separate from said rod and said implantation sheath, and a first plurality of elongated, generally filiform legs extending in a first longitudinal direction from said head portion, said legs comprising first, distal leg portions and second, intermediary leg portions disposed between said first leg portions and said head portion, wherein the first leg portions of at least some of said legs comprise substantially solid, generally flattened surfaces which bear against the wall of said blood vessel when said blood filtering medical device is in said second, radially expanded configuration, said first leg portions being devoid of means of permanent adfixture of said blood filtering medical device to the wall of said blood vessel and the width of said generally flattened surfaces, taken in a direction orthogonal to both said first, longitudinal direction and the radial direction of said blood vessel, is greater than the maximum cross-sectional dimension of said second, intermediary leg portions.

2. A blood filtering medical device according to claim 1, wherein said first leg portions are substantially plate-shaped and said second leg portions comprise at least one filament of round cross-section.

3. A blood filtering medical device according to claim 1, wherein the length of the first leg portions, in a direction parallel to said first, longitudinal direction, is less than the length, in a direction parallel to said first, longitudinal direction, of the second leg portions.

4. A blood filtering medical device according to claim 1, wherein the generally flattened surfaces of the first leg portions are curved in a direction substantially parallel to said first, longitudinal direction.

5. A blood filtering medical device according to claim 1, wherein the first and second leg portions are integral with each other.

6. A blood filtering medical device according to claim 1, wherein the second leg portions comprise pluralities of filaments of rounded cross-section.

7. A blood filtering medical device according to claim 1, wherein the first and second leg portions comprise integral plates.

8. A blood filtering medical device according to claim 7, wherein the width of said plates increases from said second leg portions toward the distalmost end of the first leg portions.

9. A blood filtering medical device according to claim 1, wherein the width of said generally flattened surfaces is between approximately 0.7 mm and approximately 1.5 mm, and the thickness of said generally flattened surfaces is between approximately 0.05 mm and approximately 0.25 mm.

10. A blood filtering medical device according to claim 1, wherein the cross-sectional dimension of the second leg portions is less than approximately 0.7 mm.

11. A blood filtering medical device according to claim 1, wherein, said first and second leg portions define therebetween an angle that is between approximately 0° and approximately 45°.

12. An intraluminal, blood filtering medical device to be implanted into a blood vessel through an implantation sheath to filter blood, said blood filtering medical device having a main axis and comprising:

filtering means having elongated legs adapted to be deployed in the blood vessel into a temporary implantation state, in which the elongated leas are exposed for filtering blood, from a radially restrained state in which said elongated legs extend substantially parallel to the main axis and in which the elongated legs are housed within the implantation sheath, said elongated legs being devoid of means for permanent adfixture to the blood vessel and having first portions adapted to contact the wall of the blood vessel when the blood filtering medical device is implanted therein and second portions, the first portions of at least some of said elongated legs having substantially solid, generally flattened surfaces adapted to bear against the wall of the blood vessel, and means for maintaining the blood filtering medical device in place in relation to the blood vessel, said means for maintaining being configured to remain sheathed within said implantation sheath while said medical device is in said temporary implantation state and configured to be completely ejected from said implantation sheath to anchor said blood filtering medical device in position in said blood vessel when permanent implantation of said blood filtering medical device is desired.

13. An intraluminal, blood filtering medical device according to claim 1, said blood filtering medical device further comprising means for maintaining said blood filtering medical device in place in relation to the blood vessel, said means for maintaining comprising a second plurality of legs extending from said head portion in a second longitudinal direction opposite to said first longitudinal direction, said second plurality of legs being configured to remain sheathed within said catheter while said blood filtering medical device is temporarily positioned within said blood vessel and configured to be ejected from said catheter to anchor said blood filtering medical device in position in said blood vessel when permanent implantation of said blood filtering medical device is desired.

\* \* \* \* \*